(12) United States Patent
Hatten

(10) Patent No.: US 8,781,306 B2
(45) Date of Patent: Jul. 15, 2014

(54) HERBAL VAPORIZER WITH ELECTRIC HEATING ELEMENT

(76) Inventor: Mark Hatten, Montclair, NJ (US)

(*) Notice: Subject to any disclaimer, the term of this patent is extended or adjusted under 35 U.S.C. 154(b) by 271 days.

(21) Appl. No.: 13/355,608

(22) Filed: Jan. 23, 2012

(65) Prior Publication Data
US 2012/0269497 A1    Oct. 25, 2012

Related U.S. Application Data

(60) Provisional application No. 61/478,285, filed on Apr. 22, 2011.

(51) Int. Cl.
*A61L 9/03* (2006.01)
*A61M 15/00* (2006.01)
*A61M 16/10* (2006.01)
*A61M 11/04* (2006.01)

(52) U.S. Cl.
CPC ........... *A61M 11/041* (2013.01); *A61M 15/00* (2013.01); *A61M 16/10* (2013.01); *A61M 16/1075* (2013.01); *A61M 2011/042* (2013.01); *Y10S 261/65* (2013.01); *Y10S 261/89* (2013.01)
USPC ........... 392/386; 392/390; 392/391; 392/393; 128/203.27; 261/DIG. 65; 261/DIG. 89

(58) Field of Classification Search
USPC .................................................. 392/391, 393
See application file for complete search history.

(56) References Cited

U.S. PATENT DOCUMENTS

| | | | | | |
|---|---|---|---|---|---|
| 1,934,887 | A | * | 11/1933 | Robinson | 128/203.27 |
| 2,047,324 | A | * | 7/1936 | Inoue | 128/203.26 |
| 2,761,055 | A | * | 8/1956 | Ike | 392/393 |
| 4,141,369 | A | | 2/1979 | Burruss | |
| 5,993,748 | A | * | 11/1999 | Wheeler | 422/125 |
| 6,095,153 | A | | 8/2000 | Kessler | |
| 6,761,164 | B2 | | 7/2004 | Amirpour | |
| 6,845,771 | B1 | * | 1/2005 | Love | 128/203.12 |
| 6,988,497 | B2 | * | 1/2006 | Levine | 128/203.27 |
| 7,475,684 | B2 | | 1/2009 | Balch | |
| 7,826,726 | B2 | * | 11/2010 | McCoy | 392/407 |
| 2007/0280652 | A1 | | 12/2007 | Williams | |
| 2013/0079733 | A1 | * | 3/2013 | Burt et al. | 604/290 |
| 2013/0098360 | A1 | * | 4/2013 | Hurmez et al. | 128/203.12 |
| 2013/0133651 | A1 | * | 5/2013 | Barker et al. | 128/203.14 |
| 2013/0247910 | A1 | * | 9/2013 | Postma | 128/203.26 |

\* cited by examiner

*Primary Examiner* — Joseph M Pelham
(74) *Attorney, Agent, or Firm* — Daniel Boudwin; Global Intellectual Property Agency LLC

(57) ABSTRACT

A smokable material vaporizer is disclosed, comprising of an enclosure having an elongated heating tube, a heating element, an air pump and a vapor collection receptacle for vaporizing a smokable material and allowing inhalation thereof. The heating tube is an elongated structure with a material loadable cap at its distal end and a screen for communicating vaporized material into the enclosure. The proximal end of the heating tube comprises a heating lamp element and a means to force air via a pump into the tube and through the screen. The heating lamp is powered by an electrical connection that includes a timer switch for safety and an activation switch. The lid of the enclosure is removable to reveal the attached heating tube, wherein smokable material is placed for the heating lamp to raise its temperature above vaporization levels, whereafter it is pumped into a collection receptacle bag for inhalation.

7 Claims, 2 Drawing Sheets

HERBAL VAPORIZER WITH ELECTRIC HEATING ELEMENT

CROSS REFERENCE TO RELATED APPLICATION

This application claims the benefit of U.S. Provisional Application No. 61/478,285 filed on Apr. 22, 2011, entitled "JarHead."

BACKGROUND OF THE INVENTION

1. Field of the Invention

The present invention relates to vaporizers and smoking devices. More specifically, the present invention relates to an herbal vaporizer utilizing a halogen heat source and an air pump to extract vapor from the herbal substance for collection in a container for later inhalation.

Vaporizing is a process by which a product is communicated from a source material to a user through the vapor carrier. This is useful for medicinal, therapeutic and relaxation purposes, wherein a product may be carried through a cloud of vapor rather than directly applied, combusted or otherwise communicated to a user. The active ingredient is released into the vapor for the user to inhale or be placed in contact with, depending on the ingredient and the desired effect. In the case of tobacco and medicinal herbal remedies, the user is allowed access to the active ingredients through the vapor carrier rather than through the process of combustion and inhalation of the byproducts that are associated therewith. In the case of aromatherapy materials, the active ingredient is vaporized into the air for the user to absorb or inhale as desired.

Vaporizers are devices that facilitate the extraction of active ingredients from a product without combustion or burning thereof. Vaporizers are utilized to raise the temperature of a product above its vaporization temperature, wherein the active ingredient boils from the material substrate and enters the air as a gaseous vapor. The base product or substrate does not ignite, combust or develop smoke. This method of extraction is considered far healthier for the user, as noxious smoke otherwise generated during combustion is absent from the vapor, along with the associated tar and other carcinogenic byproducts resulting from normal burning and ignition methods. The vapor can be inhaled or enjoyed by the user without the byproducts that are otherwise created using traditional methods of material burning to release the ingredients or flavors. The released vapor is also cooler that its smoke counterpart, which is softer and less dangerous for the user's respiratory system during inhalation. The immediate environment is also not exposed to the noxious smoke that develops from burning.

Vaporizer devices themselves are structures that employ familiar design features for the purpose of raising a source material temperature above its vaporization level to release its active ingredients without initiating combustion. These devices generally include a bore or venturi for extracting the vapor from a contained product, a heating source for heating the product material through conduction, convection or radiative heat transfer, and finally a means to collect the extracted vapor for direct or later inhalation. These devices have varying assembly components, construction and operation. Some devices can be extremely expensive and sophisticated, while others can be of simple construction at the expense of efficiency or quality. The present invention provides a vaporizer device that provides a simply constructed apparatus that is highly effective at extracting an active ingredient from a smokable product using a heat lamp, air pump and collection means for gathering the released vapor. Its design is simple and easy to produce, and therefore is less expensive when compared to similar devices.

2. Description of the Prior Art

Patents have been issued and applications published for various vaporizer devices in the prior art. These devices vary in complexity and function, ranging from very intricate and expensive assemblies to simple enclosures with a heat source. The present invention provides a new vaporizer that includes a heater stack configuration using a heating bulb, an air pump for moving air through the enclosure and an extraction hose for collecting the developed vapor. A timer controlled power switch further prevents overheating if left unaccompanied, requiring less diligence by the user in operation. The following devices are considered the most relevant to the present invention, and include devices that substantially divergent in both structural elements and spirit from the present invention.

U.S. Pat. No. 4,141,369 to Burruss is one such disclosure that comprises an electrical device for the non-combustion utilization of smoking materials having a canister in which air is electrically heated to volatilize the smoking materials within a receptacle housed in a mouthpiece. As the user draws on the mouthpiece, heated air and volatilized smoking material is drawn into the user's mouth. The canister houses a light bulb for heating the material using electrical power, wherein convection heating from the canister and into the mouthpiece is naturally flowing and assisted by the user drawing therefrom. The present invention utilizes an air pump to assist the evacuation of vaporized material from a container to a receptacle, whereafter it can be inhaled by the user at his or her pleasure.

Another such device is U.S. Pat. No. 6,761,164 to Amirpour disclosing an herbal vaporizer device having a fire-resistant housing forming a heat generating compartment having an access opening and an elongated heating element. A connector is include to electrically connect the heating element to a power source, while a hand piece is used in conjunction with the access opening and heating element to position an herbal substance in proximity to the heat source to begin vaporization. The Amirpour device utilizes an external support for the target substance being vaporized and further does not provide a means to create a forced air flow over the substance. The present invention provides an enclosed assembly that houses the vaporizing material, allows for an air pump to force heat over the material and evacuate the enclosure of the created vapor.

U.S. Pat. No. 6,095,153 to Kessler describes a vaporizing device that is adapted to provide a heating system that is capable of maintaining a temperature within a +/−10 degree Celsius range. A source material holder, a heating element and a flow control means is provided for volatilizing the material without combustion or significant denaturing thereof. The Kessler device, while providing an air flow means, does not disclose the enclosure and elongated heating element of the present invention, nor the steps for its use in vaporizing a source material.

U.S. Pat. No. 7,475,684 to Balch describes a vaporizer apparatus for vaporizing medicinal herbs utilizing a housing, a heating element, a shield and an opening for extracting the released material vapor. The shield comprises a tapered end that has an opening to allow the passage of a drawn air over the product. A hand piece is utilized in conjunction with the Balch device, in a similar fashion to the Amirpour, for collecting or inhaling the vaporized material from the housing. The present invention utilizes an air pump and collection receptacle for extracting the vapor from an enclosure.

Finally, U.S. Patent Application Publication No. 2007/0280652 to Williams discloses an improved vaporizer unit with improved airflow to provide thick vapor clouds. The device employs passageway components and apertures with sufficient diameter to allow swift and smooth airflow draw, as well as a halogen bulb heating element for vaporizing the source material active ingredient. The Williams device provides a vaporizer structure that significantly diverges from the present invention, which provides an enclosure, heating tube and forced air flow means for extracting vapor from a source material positioned within the heating tube.

It is therefore submitted that the present invention substantially diverges in design elements from the prior art and consequently it is clear that there is a need in the art for an improvement to existing vaporizer devices. In this regard the instant invention substantially fulfills these needs.

SUMMARY OF THE INVENTION

In view of the foregoing disadvantages inherent in the known types of vaporizer devices now present in the prior art, the present invention provides a new vaporizer wherein the same can be utilized for providing convenience for the user when raising the temperature of a smokable or aromatic material without initiating combustion.

It is therefore an object of the present invention to provide a new and improved vaporizer device that has all of the advantages of the prior art and none of the disadvantages.

Another object of the present invention to provide a vaporizer device having an enclosure, a heater tube, a forced air means, collection receptacle and an electrical heating means.

Another object of the present invention is to provide device that forces heated air over the target media to initiate vaporization of its active ingredient.

Yet another object of the present invention is to provide an electric power source that is controlled by a timer switch to prevent overheating.

A final object of the present invention is to provide a vaporizer device that is inexpensive to produce and easily manufactured.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
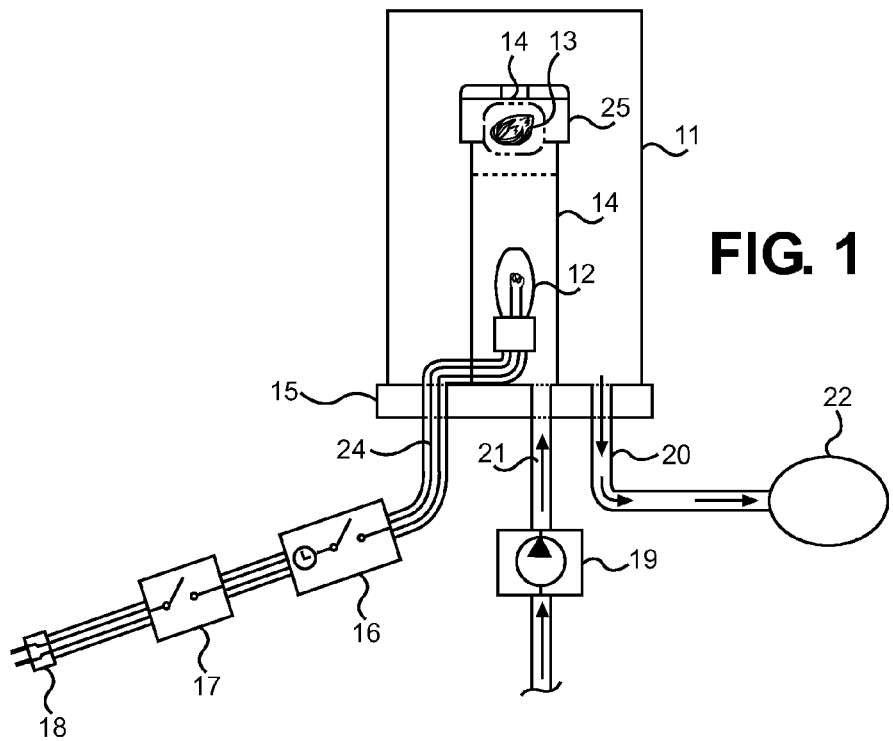
FIG. 1 shows a schematic view of the elements of the present vaporizer device.

Reference is made herein to the attached drawings. Like reference numerals are used throughout the drawings to depict like or similar elements of the vaporizer device. For the purposes of presenting a brief and clear description of the present invention, the preferred embodiment will be discussed as used for vaporizing a target material without initiating combustion or ignition. The figures are intended for representative purposes only and should not be considered to be limiting in any respect.

Referring now to FIG. 1, there is shown a schematic view of the vaporizer device of the present invention. The device comprises an enclosure 11 forming a closed vessel for containment of the vapor generated during the device heating operation, sealed by a removable lid structure 15 that provides a plurality of apertures and support for elements that control device operation. A heater tube 14 protrudes from the lid 15 and into the enclosure. The heater tube 14 is a hollow, conductive member that communicates thermal load from an electrical heating source to a vessel cap 25 at its distal end for heating a source material to the vaporization temperature of its active ingredient. The vessel cap 25 within the distal end of the heater tube is a removable cap that is filled with a source material 13 and reattached to the tube 14 prior to operating the device. The cap 25 comprises an open end that engages the tube 14 and an opposite end having a screen aperture 14, allowing vapor to escape therethrough and into the enclosure 11 interior volume.

Along the proximal end of the heater tube 14, which is affixed to the enclosure lid 15, is an electrical heating source 12. The preferred heating source is a halogen bulb that generates thermal heat generation through electrical resistance. As the bulb begins to heat up, heat travels through the tube hollow interior and along its tubular sidewalls to raise the source material temperature above its vaporization temperature. An electrical connection 24 is provided for the heating source through the enclosure lid 15. The connection 24 distributes power from an A/C or battery power source through a hot and neutral wire. Along the wire are two switches, a first power switch 17 that is user operates to control the flow of current to the bulb 12, and a second timer switch 16 that automatically opens the connection and turns off the bulb after a given time period in operation. The timer switch 16 is provided to prevent prolonged heat exposure to the source material 13 and the elements of the device, which is potential fire hazard if left unoccupied or monitored. The timer automatically shuts off the device without user interaction, allowing the user to enjoy the device without worrying about its potential hazards if not diligently monitored.

A second aperture through the enclosure lid is a passageway to attach an air flow means. Air is forced through a connector tube 21, through the second aperture in the lid and into the heater tube 14. An air pump 19 supplies the motive force to pressurize the incoming air and force it through the heater tube, carrying the bulb heat and forcing vapor to escape from the source material 13 and through the heater tube screen 14. The air pump facilitates the vapor exiting the heater tube distal end, entering the enclosure and exiting through a third aperture connecting to a collection receptacle 22 via a connecting tube 20. The vapor is forced into the receptacle 22, or is optionally directly drawn by the user. Using a receptacle, such as an expandable bag or similar device, the vapor can be collected in a common location and inhaled or otherwise utilized from the receptacle while the heating element 12 can be deactivated.

Figure 2:
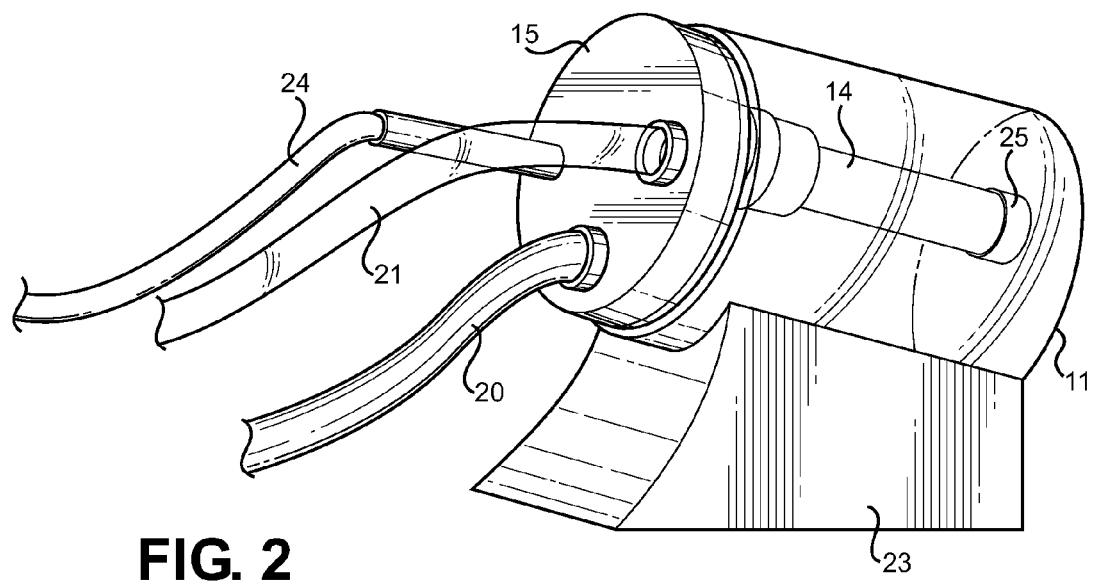
FIG. 2 shows a frontal perspective view of the present vaporizer device in a working position.

Referring now to FIG. 2, there is shown a side perspective view of the present vaporizer device of the present invention. As shown, the enclosure 11 is a hollow member adapted to contain the heater tube 14 and vapor exiting from the tube distal end, through the tube cap 25. To operate the device, the lid 15 is removed from the enclosure 11, wherein access to the heater tube 14 and its end cap 25 are provided. The end cap 25 is removed to reveal a location for loading a source material therein. The cap 25 is then replaced on the tube distal end, and the lid 15 is replaced onto the enclosure 11. The electrical connection 24 that provides power to the internal heating element within the heater tube 14 is then turned on, plugged in or otherwise activated. The heating element, which is preferably a halogen bulb, begins to generate heat that travels down the length of the heater tube 14 to begin raising the source material temperature. While this is occurring, an air pump tube 21 is connected to the lid through a second aperture, wherein a pump may be activated to begin forcing air into the enclosure. A vapor collection tube 20 is connected to a third aperture for transferring the vapor from the enclosure and into a receptacle as desired, once the pump is initiated.

Alternatively, a user may draw directly from the third aperture without collecting the source material vapor beforehand. This alternate means of drawing vapor from the enclosure eliminates the collection bag, and the use of the air pump if so desired. The user may utilize an elongated tube or directly draw from the third aperture to inhale the vapor. When the air pump is utilized, air is forced through the heater tube 15 and over the source material contained within the tube end cap 25, through the end cap screen and into the enclosure before exiting through the lid third aperture. During the vaporization and drawing process, the enclosure may be supported by a stand device 23 that supports the enclosure in a position such that the tubes and connections along the enclosure lid are not dislodged or pulled away from the lid.

Figure 3:
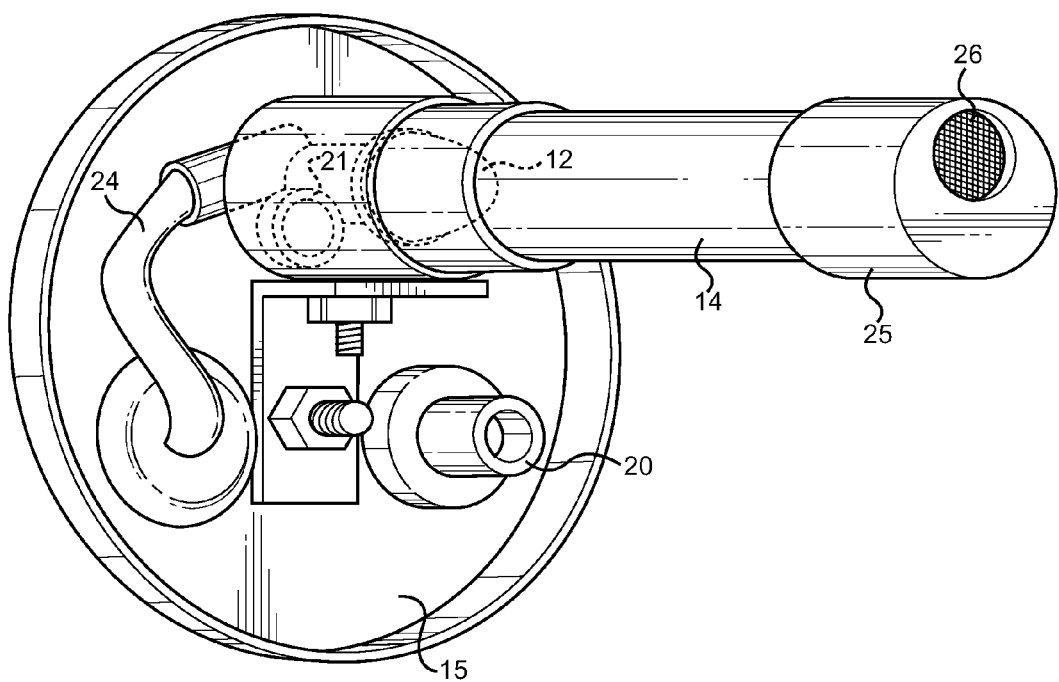
FIG. 3 shows the functional aspects of the present vaporizer enclosure lid.

Referring now to FIG. 3, there is shown a perspective view of the enclosure lid 15 and it's attached elements that operate the disclosed vaporizer device. The lid supports an elongated heater tube 14 via a bracket such that the heater tube is perpendicularly mounted to the lid and aligned with the air pump aperture 21. Alternatively, the heater tube and lid may be of unitary construction. In this embodiment, thermal insulation or an air gap may be necessary between the lid 15 and tube 14 to prevent the heating element 12 from heating the lid during operation, which may be a burn risk to a user. The three apertures through the lid are provided for the electrical connection 24 to reach the heating element 12 within the heater tube 14, to provide a means to force air into the heater tube 14 via an air pump inlet 21, and finally a means to draw vapor from the enclosure interior through a final aperture 20. The apertures are adapted to make a sealed connection between their connecting elements, most notably the electrical connection 24 and the air input 21 and outlet 20 tubes. In this way, unauthorized vapor leakage is not permitted through these apertures, and the vapor is controlled within the enclosure before being communicated to a user or receptacle.

The air pump of the present invention provides a means to draw a large quantity of vapor from a source material during operation, and collect the vapor into a receptacle for later use. Rather than requiring a user to manually draw from the device, the pump facilitates the vapor exiting the enclosure for later application or enjoyment. The heater tube is preferably a conductive material such as copper or similar metallic material, while the enclosure may be an insulator such as glass or similar transparent material. The electrical elements of the device provide safeguards for the device, such that the device may be left unoccupied without the threat of creating a fire hazard. Overall, the present invention provides an advancement in the air of vaporizer devices, and one that is simply constructed and easily assembled. This provides an advantage over larger, more complicated and expensive vaporizer devices, wherein more individuals may have access to such a device for medical and therapeutic purposes.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A source material vaporizer device, comprising:
an enclosure having an interior volume and a lid to seal said interior volume;
an elongated heater tube having a distal end and a proximal end, said proximal end mounted against said lid and having a heating element to raise said source material temperature;
said heater tube distal end providing a location to place a said source material and communicate vapor therefrom into said enclosure;
said lid further comprising a first, second and third aperture, said second aperture aligned with said heater tube proximal end;
an electrical connection traveling through said first aperture and to said heating element to provide a source of power, said connection having a power switch and a timer switch to control current through said connection and to said heating element;
said third aperture adapted to draw vapor from said enclosure.

2. The device of claim 1, further comprising an air pump and air tube connecting to said second aperture for forcing air through said heater tube and into said enclosure and out of said third aperture.

3. The device of claim 1, wherein said third aperture connects to a vapor receptacle as said air pump forces air from said enclosure and into said receptacle.

4. The device of claim 1, wherein a user manually draws from said third aperture for direct utilization of said vapor.

5. The device of claim 1, further comprising a stand such that said enclosure can be positioned into an operational position without manual manipulation and said aperture connections remain intact.

6. The device of claim 1, wherein said aperture connections further comprise air tight seals to prevent vapor leakage.

7. The device of claim 1, wherein said heater tube comprises a conductive material to communicate conductive heat to said source material.

* * * * *